United States Patent [19]

Batchelder

[11] Patent Number: 4,740,708
[45] Date of Patent: Apr. 26, 1988

[54] SEMICONDUCTOR WAFER SURFACE INSPECTION APPARATUS AND METHOD

[75] Inventor: John S. Batchelder, Tarrytown, N.Y.

[73] Assignee: International Business Machines Corporation, Armonk, N.Y.

[21] Appl. No.: 719

[22] Filed: Jan. 6, 1987

[51] Int. Cl.$^4$ .................................. G01N 21/88
[52] U.S. Cl. ........................ 250/563; 250/572; 356/237
[58] Field of Search ............ 250/572, 562, 563; 356/237, 239, 430, 431

[56] References Cited

U.S. PATENT DOCUMENTS

| | | | |
|---|---|---|---|
| 4,004,153 | 1/1977 | Obser et al. | 250/572 |
| 4,265,545 | 5/1981 | Slaker | 356/431 |
| 4,441,124 | 4/1984 | Heebner et al. | 358/106 |
| 4,449,818 | 5/1984 | Yamaguchi | 358/237 |
| 4,468,120 | 8/1984 | Tanimoto et al. | 356/237 |
| 4,601,576 | 7/1986 | Galbraith | 250/563 |
| 4,626,101 | 12/1986 | Ogawa et al. | 250/563 |

OTHER PUBLICATIONS

IBM Technical Disclosure Bulletin, "Patterned Wafter Scanner", J. S. Batchelder, vol. 27, No. 10B, Mar., 1985, pp. 6273–6275.

Primary Examiner—Edward P. Westin
Attorney, Agent, or Firm—Perman & Green

[57] ABSTRACT

A system and procedure for the inspection of the surface of a semiconductor wafer ascertains that particulate contaminants have been adequately cleaned from the surface during the manufacture of integrated electric circuits. The wafer is advanced in a first direction and is optically scanned in a second direction, transverse to the first direction, for recording intensities of light reflected normally from the wafer surface as a function of location on the scan line. A high intensity reflection is indicative of a smooth flat surface suitable for inspection of particles by an integrating hemisphere with plural photodetectors therein. A weak reflection is indicative of undulations and patterned regions which are unfavorable for examination of particles on the wafer surface. A second scan is offset sideways to compensate for motion of the wafer so as to rescan the same line as the first scan. The photodetectors in the integrating sphere are gated on and off during the second scan at the locations of suitable inspection sites determined from the first scan.

22 Claims, 5 Drawing Sheets

SEMICONDUCTOR WAFER SURFACE INSPECTION APPARATUS AND METHOD

BACKGROUND OF THE INVENTION

This invention relates to a system and procedure for inspection of a surface of a workpiece and, more particularly, to the inspection of the surface of a semiconductor wafer for contamination by particles which may develop in the manufacture of integrated electric circuits.

Integrated circuits are manufactured on relatively large wafers which are cut by a saw to separate the individual circuit chips. Portions of the surface of the wafer may be built up with layers of material and may also be etched, particularly at the sites of circuit chips, to impart a pattern to the surface, which pattern is characterized by undulations in the wafer surface. Other portions of the wafer surface, particularly regions between the circuit chips reserved for the kerf of the saw, the saw-cut regions being the kerf, may be bare of an undulation pattern and have the characteristics of a specularly smooth surface.

During the process of manufacturing the wafers, it is a common occurrence for particles of various materials employed in the manufacturing process to come to rest upon the wafer surface. Such particles alight on both the smooth and the patterned portions of the surface of a wafer. Such particles act as a contaminant, and would interfere with the proper operation of the electric circuits if allowed to remain on the surface. Accordingly, one step in the manufacturing process is the cleaning of the wafer surfaces to remove particulate contamination. Thereafter, it is necessary to inspect the wafer surfaces to insure that they have been cleaned adequately of the contamination.

Of particular interest herein is inspection of a wafer surface by optical inspection equipment. The operation of such equipment is based on the observation that a reflection of illuminating light from a wafer surface depends on the direction of illumination relative to the wafer surface, and also on physical characteristics of the surface. Specific physical characteristics of the surface affecting reflection of the illuminating light are smooth regions, undulating regions, and particles. The smooth regions can produce high intensity reflections in a specific direction. The undulating regions can produce both strong reflected signals at specific angles as well as intense scatter in many directions. A particle induces a reflection which is relatively weak and is scattered in many directions.

A problem arises in that equipment which has been configured to process the weak scattered reflected light from a particle can be rendered inoperative by exposure to the intense scatter from a smooth or patterned region. In the case of a smooth surface region, free of undulations and illuminated by a beam of light normal to the surface, a path of reflected light can be predicted because it is known that the reflected light will be also normal to the surface. However, the problem of dealing with reflected light is compounded in the case of the undulations of a patterned region because the surface thereof can reflect light in any one of many possible directions depending on the local orientation of a part of the surface receiving an incident beam of illuminating light.

To avoid excessive reflected light in the use of optical inspection equipment, one form of equipment illuminates the wafer surface normally, and views reflected light at a glancing angle by light detectors positioned at or near the surface. Another form of equipment provides for a viewing of a surface defect along a normal to the surface in response to both horizontal and vertical illumination of the subject.

SUMMARY OF THE INVENTION

The foregoing problem is overcome and other advantages are provided by a procedure and apparatus, in accordance with the invention, for optically scanning a wafer to determine the locations of surface regions suitable for the inspection of particulate contaminants and, by use of the same scanning apparatus, to examine the surface for particles. Scanning is accomplished in two dimensions by physically moving the wafer in a longitudinal direction by a conveyor, and by optically scanning the wafer surface in a transverse direction perpendicular to movement of the conveyor. A feature of the invention is the repetition of a transverse scan, without interruption of the conveyor motion, whereby suitable inspection sites are selected during the first of a pair of transverse scans and inspection of the selected sites is accomplished during the second of the pair of transverse scans. The repetition of the scan is accomplished in a preferred embodiment of the invention by use of an acousto-optic modulator which offsets the path of a transverse scan to compensate for displacement of the wafer by the conveyor.

Surface information is obtained during the first of the two transverse scans by illumination of the surface with a light beam directed by a lens assembly normally to the surface followed by retroreflection via the lens assembly to a beam splitter and focusing optics. A reflecting hemisphere is placed between the surface and the lens assembly to enclose the portion of the wafer being viewed, the hemisphere having a central slot for admitting the scanning beam to the surface. Particle information is obtained during the second of the two transverse scans by plural photodetectors extending into the sphere for sensing the presence of light scattered by a particle about the inside of the sphere. Electronic circuitry is provided for memorizing the locations of suitable inspection sites, having smooth surface regions, obtained during the first transverse scan, and for activating the photodetectors only when these sites appear during the second transverse scan so as to protect the photodetectors from the intense light of the patterned regions. It is assumed that the distribution of the particles is substantially uniform over the entire wafer surface so that a sampling of particles only in the smooth surface regions is representative of the adequacy of the entire wafer cleaning operation.

BRIEF DESCRIPTION OF THE DRAWING

The aforementioned aspects and other features of the invention are explained in the following description, taken in connection with the accompanying drawing wherein.

DETAILED DESCRIPTION

Figure 1:
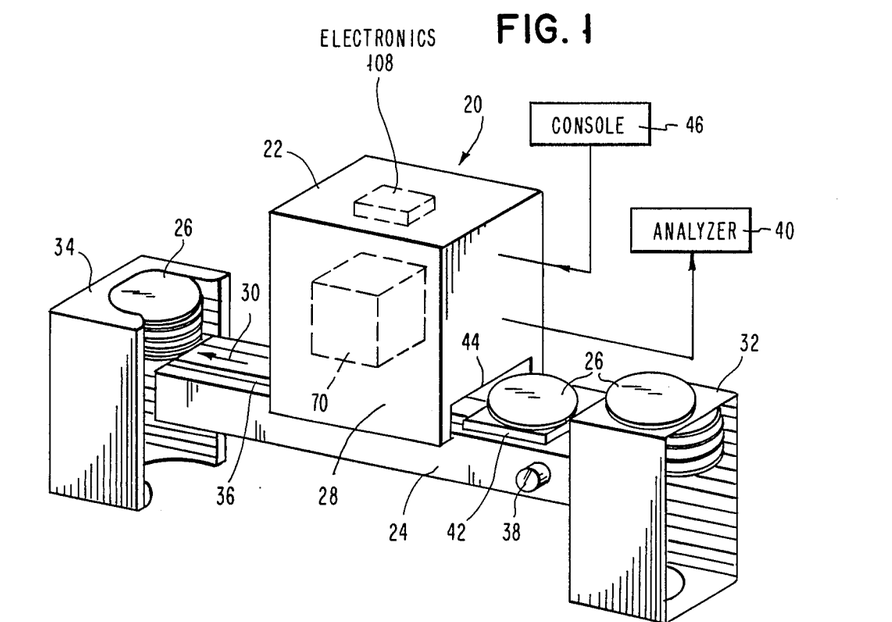
FIG. 1 is a stylized view of an inspection system of the invention, including wafers carried by a conveyor past an inspection station.

With reference to FIG. 1, there is shown a surface inspection system 20 which is constructed in accordance with the invention. The system 20 comprises an optical scanner 22 and a conveyor 24 which carries semiconductor wafers 26 to an inspection station 28 within the scanner 22. The conveyor 24 moves the wafers 26 in the direction of an arrow 30 from an input cassette 32 to an output cassette 34 via the scanner 22, the wafers being carried along a track 36 which moves continuously during inspections of the wafers 26 by the scanner 22. The conveyor 24 includes a motor 38 which drives the track 36 at a speed selectable by a person operating the system 20.

The system 20 provides for the sequential inspection of the wafers 26 in automatic fashion. The wafers 26 are applied, one at a time, to the scanner 22 which scans the surfaces of the respective wafers 26, in accordance with the invention, to locate particulate contamination on these surfaces. The results of the surface inspection of each of the wafers 26 is displayed on an analyzer 40 of optical signals generated within the scanner 22, as will be described hereinafter.

Each wafer 26 obtained from the input cassette 32 is secured in position on the moving track 36 by a vacuum chuck 42 (one of which is shown in FIG. 1) the chuck 42 being carried by the track 36 through the inspection station 28. The scanner 22 is provided with two light traps, one light trap 44 being located at an input side of the scanner 22, and the second light trap (not shown) being located at the output side of the scanner 22. The light traps 44 prevent entry of external light to the interior of the scanner 22, and also prevent egress of laser light from the scanner 22 so as to protect personnel from the laser light. Also included within the system 20 is a console 46 by which an operator can activate the scanner 22 and the conveyor 24.

Figure 2:
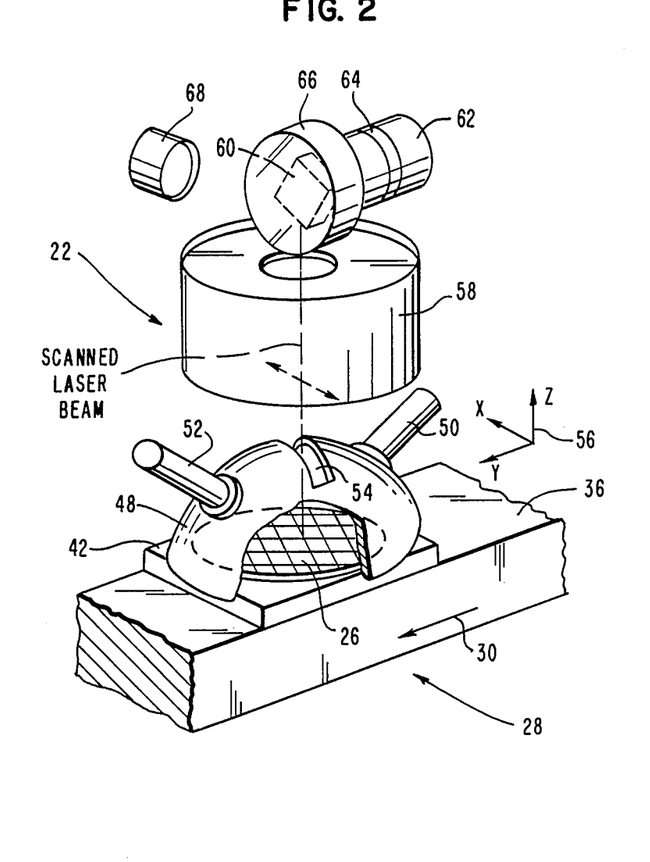
FIG. 2 is a partial isometric view of an optical system included within the inspection system of FIG. 1.

With reference also to FIG. 2, there are shown components located within the interior of the scanner 22. The scanner 22 comprises an optical integrating hemisphere 48 having two optical detectors 50 and 52, mounted thereon and extending to the interior of the hemisphere 48 for viewing light scattered from a particle on the surface of a wafer 26. In a preferred embodiment of the invention, the detectors 50 and 52 are constructed as photomultiplier tubes which can be gated on and off by an electrical signal. Thereby, the detectors 50, 52 can be activated for viewing scattered light from a particle on the surface of a wafer 26 while being deactivated, so as to protect the detectors 50, 52 from high intensity light which may be reflected towards the detectors 50, 52 by undulations in a patterned region of the wafer surface.

The hemisphere 48 is positioned above the track 36 a sufficient distance to clear the chuck 42 and the wafer 26 within the inspection station 28 as shown in FIG. 2. The diameter of the hemisphere 48 is sufficient to permit the hemisphere 48 to enclose the portion of the upper surface of the wafer 26 being inspected at the station 28. The hemisphere 48 is provided with a slot 54 oriented transversely to the direction of movement of the track 36, the slot 54 having a sufficient length to allow entry of a scanning laser beam for illuminating the wafer 26. The hemisphere 48 is provided with a white highly-reflectant surface for integrating light scattered from a particle on the wafer surface, and for reflecting the scattered light to the detectors 50 and 52. A set of coordinate axes 56 shows X,Y and Z axes, the mechanical motion of the wafer 26 being along the Y axis and the optical scanning of the laser beam being along the X axis in a plane parallel to the Z axis. Thereby, the scanner 22 and the conveyor 24 cooperate to perform a two-dimensional scan of the surface of a wafer 26.

Also shown in FIG. 2 is a portion of an optical system of the scanner 22, which optical system will be described in further detail in FIG. 3. The portion of the optical system shown in FIG. 2 includes a telecentric scan lens 58, a rotating polygon mirror 60 (shown in phantom), a motor 62 which rotates the polygon mirror 60, a shaft-angle encoder 64 which is mechanically coupled to the motor 62 and the mirror 60 for outputting an electric signal indicating angular position of the mirror 60, a sealed housing 66 which encloses the polygon mirror 60 and supports the motor 62 and the encoder 64, and a collimating lens 68. The collimating lens 68 directs laser light towards the rotating polygon mirror 60 which, in turn, redirects the laser light as a scanned laser beam through the scan lens 58 and the slot 54 to the surface of the wafer 26. The scan lens 58 is positioned above the hemisphere 48 for directing and focusing the scanned beam through the slot 54 to the wafer surface.

Figure 3:
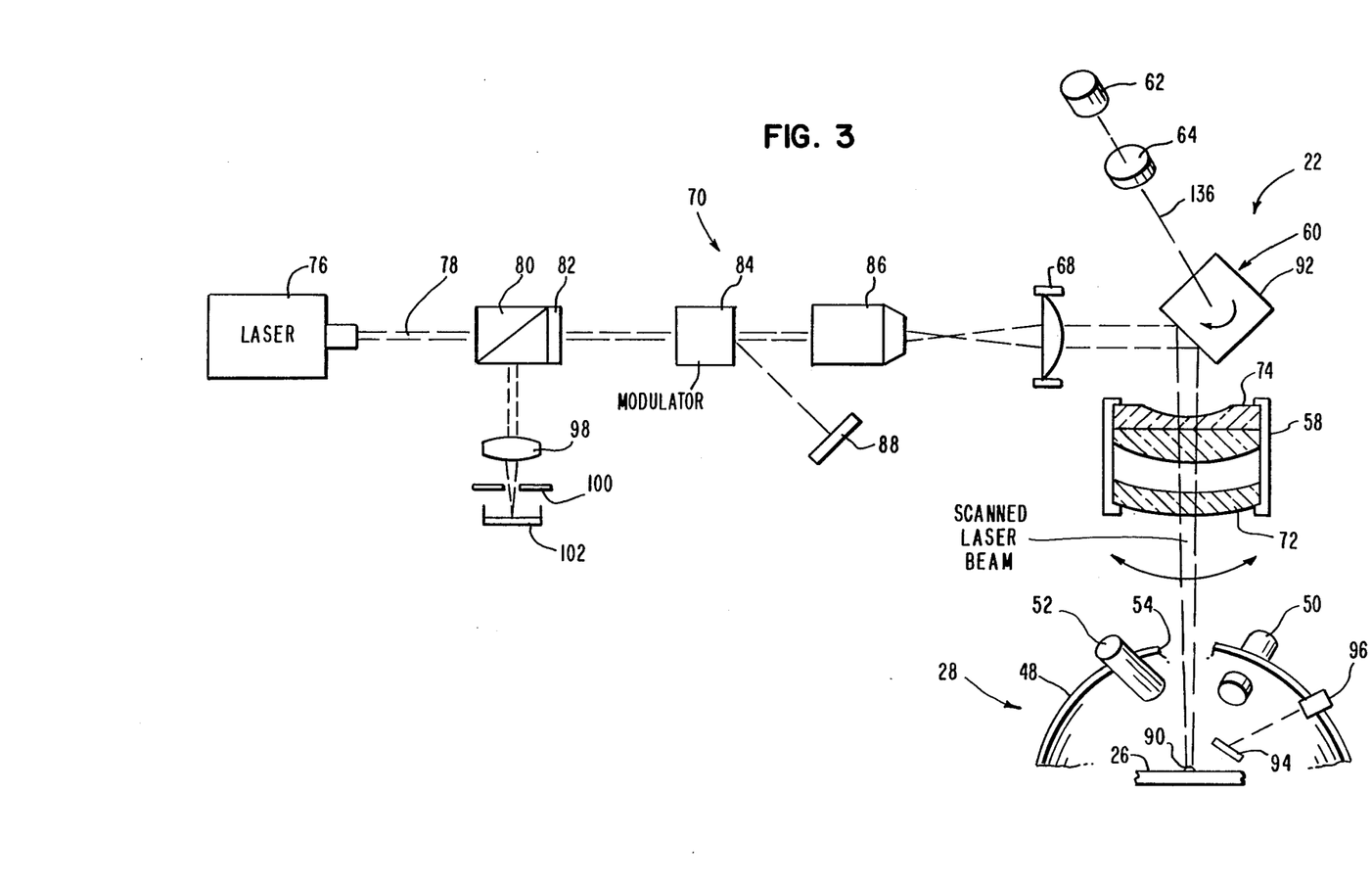
FIG. 3 is a schematic diagram of the optical system.

FIG. 3 shows an optical system 70 of the scanner 22 (also indicated in phantom in FIG. 1). A portion of he components of the optical system 70 have already been described in FIG. 2, these components being the collimating lens 68, the polygon mirror 60, the scan lens 58, and the hemisphere 48 with its slot 54 and detectors 50 and 52. The scan lens 58 is shown to comprise, by way of example, a front lens element 72, and a rear doublet lens element 74. The optical system 70 further comprises an argon ion laser 76 which produces a 10 milliwatt beam 78 of radiation at a wavelength of 4880 angstroms. The beam 78 is linearly polarized and passed through a polarizing beam splitter 80 and a quarter-wave plate 82 which transforms the beam into circularly polarized light. The circularly polarized light is preferred because the circular polarization improves detectability of small particles as compared to plane polarized light. The beam then passes through an acous-to-optic modulator 84 which deflects approximately 90% of the beam into a first order Bragg diffraction angle which passes into a microscope objective 86. The remaining 10% of the light of the beam is deflected into a beam stop 88.

The light passing through the objective 86 comes to a focus and then expands to fill the collimating lens 68. Rays of the beam are made parallel by the collimating lens 68 resulting in a beam being outputted by the collimating lens 68 with a diameter which is preferably approximately 30 millimeters in the preferred embodiment of the invention. The beam outputted by the collimating lens 68 strikes the rotating polygon mirror 60 and is reflected by the mirror 60 into a flat field of the telecentric scan lens 58. The lens 58 focuses the beam to a focal spot having a diameter of preferably 12 microns, the focal spot being at the location of a contaminating particle 90 on the top surface of the wafer 26.

As each facet 92 of the mirror 60 rotates past the incident laser beam, another scan line is generated upon the surface of the wafer 26. While various rotation speed of the mirror 60 are possible, in the preferred embodiment of the invention, the mirror 60 rotates at approximately 250 revolutions per second, generating approximately 1000 scan lines per second in the case of the four sided polygon depicted for the mirror 60 in FIG. 3. If the mirror 60 were shaped as an octagon instead of the square depicted in FIG. 3, then the number of scan lines would be doubled to 2,000 scan lines per second. At the beginning of each new sweep of the laser spot across the surface of the wafer 26, the laser beam is deflected within the hemisphere 48 by a mirror 94 into a photodetector 96 which may comprise a photodiode. The mirror 94 is secured to the hemisphere 48 by an armature (not shown). The photodetector 96 produces an electric pulse signalling the beginning of a new line scan.

The optical system 70 further comprises a lens 98, a pinhole 100, and a light detector 102 for viewing light reflected normally from the surface of the wafer 26 back through the scan lens 58 towards the laser 76. Thus, there are three sets of optical sensing devices which sense light of the laser 76 reflected from the wafer 26, as follows. The detectors 50 and 52 in combination with the reflecting inner concave surface of the hemisphere 48 sense scattered rays of light reflected from a particle, such as the particle 90 on the surface of the wafer 26. Light reflected by a flat smooth region of the wafer surface is sensed by the detector 102. Light at an extreme end position of the scanned laser beam is intercepted by the mirror 94 and directed to the photodetector 96 to indicate that another scan line is to be initiated by the rotating polygon mirror 60.

In operation, the sites of the wafer surface that are to be inspected for particulates, are structured as bare film or silicon that have a higher specular reflection coefficient than the rest of the wafer surface. These sites are detected as follows. Since the scan lens 58 is telecentric, light striking a mirror-like surface on the wafer 26 is retro-reflected off of the wafer surface, back through the scan lens 58, and off of the rotating mirror 60 to produce a collimated beam proceeding along the same path as the incident beam 78 generated by the laser 76. The retro-reflected beam passes through the collimating lens 68, is focused through the objective 86, is up-shifted in position by the acousto-optic modulator, and then passes through the quarter-wave plate 82. At this point the light is linearly polarized in a direction which is rotated 90 degrees with respect to the initial polarization of the retro-reflected light, this resulting in a deflection of the retro-reflected light by the polarizing beam splitter 80 into the lens 98. The retro-reflected light is directed by the lens 98 towards the pinhole 100 which pinhole is located at one focal length from the lens 98. The arrangement of the lens 98 and the pinhole 100 is confocal, and operates such that only light reflecting off of the wafer surface is at such an image distance that the retro-reflected light is reimaged through the pinhole 100 onto the detector 102. The pinhole 100 prevents transmission of retroreflected light to the detector 102 from retroreflections which may occur from surfaces other than the wafer surface such as, by way of example, surfaces of the various lenses of the system 70, a surface of the chuck 42, as well as other false indications of reflected light. The detector 102 may be constructed as a PIN diode for producing an electric signal proportional to the specular reflectivity of the portion of the wafer surface being illuminated by the laser beam. Thereby, the pinhole 100 prevents false indications of light from inducing a signal from the detector 102.

The acousto-optic modulator is activated by an electric signal as will be described subsequently with reference to FIG. 4, and generates an acoustic wave which interacts, in the manner of an optical grating, with the laser beam to offset the direction of rays of light passing through the modulator 84. Such offset alters the location of the beams incident and reflected from a facet of the polygon mirror 60, as well as the site of the scan line of the laser beam illuminating the wafer surface. With reference to the coordinate axes 56 of FIG. 2, the offset of the scan line is opposite to the direction of motion of the conveyor track 36, and is thus an offset along the Y axis. The offset is a sideward shifting of the position of the scan line which is parallel to the X axis.

For example, on even scan lines, the modulator 84 is operated at an acoustic frequency of 77.23 megahertz which operating frequency produces a deflection in the illuminating beam of 2.744 degrees. On odd scan lines, the modulator 84 is operated at an acoustic frequency of 77.25 megahertz, which operating frequency produces a beam deflection of 2.745 degrees. As a result, even scan lines on the wafer surface are displaced 6 microns with respect to the position of the odd scan lines.

Figure 5:
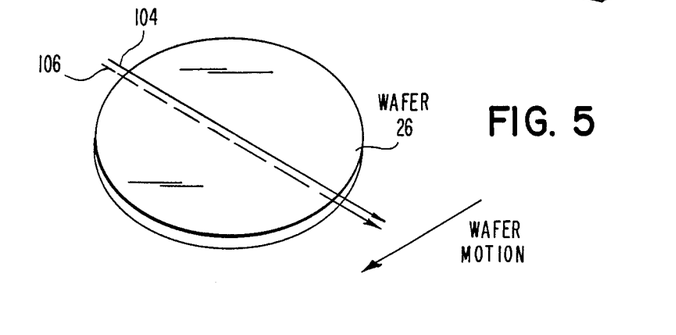
FIG. 5 shows a wafer with a pair of scan lines indicated diagrammatically, one scan line being offset to compensate for translation of the wafer.

The offsetting of the foregoing even and odd scan lines is demonstrated in FIG. 5 wherein an even scan line 104 is shown as a solid line and an adjacent shifted even-scan line 106 is shown as a dashed line. The amount of shifting of the scan lines is dependent on the selection of acoustic frequencies at the modulator 84. The frequencies are selected in accordance with the selection of speed of the conveyor track 36 such that the amount of offset is equal to the amount of travel of the wafer 26 between scan lines. Thus, in the case of the foregoing example of the preferred embodiment of the invention wherein the offset is 6 microns per scan the movement of the wafer 26 along the Y axis during the time interval from the beginning of one scan to the beginning of the next scan is also 6 microns. The action of the modulator 84 is therefore to produce pairs of overlapping scan lines, such that every other scan is 12 microns apart.

Figure 4:
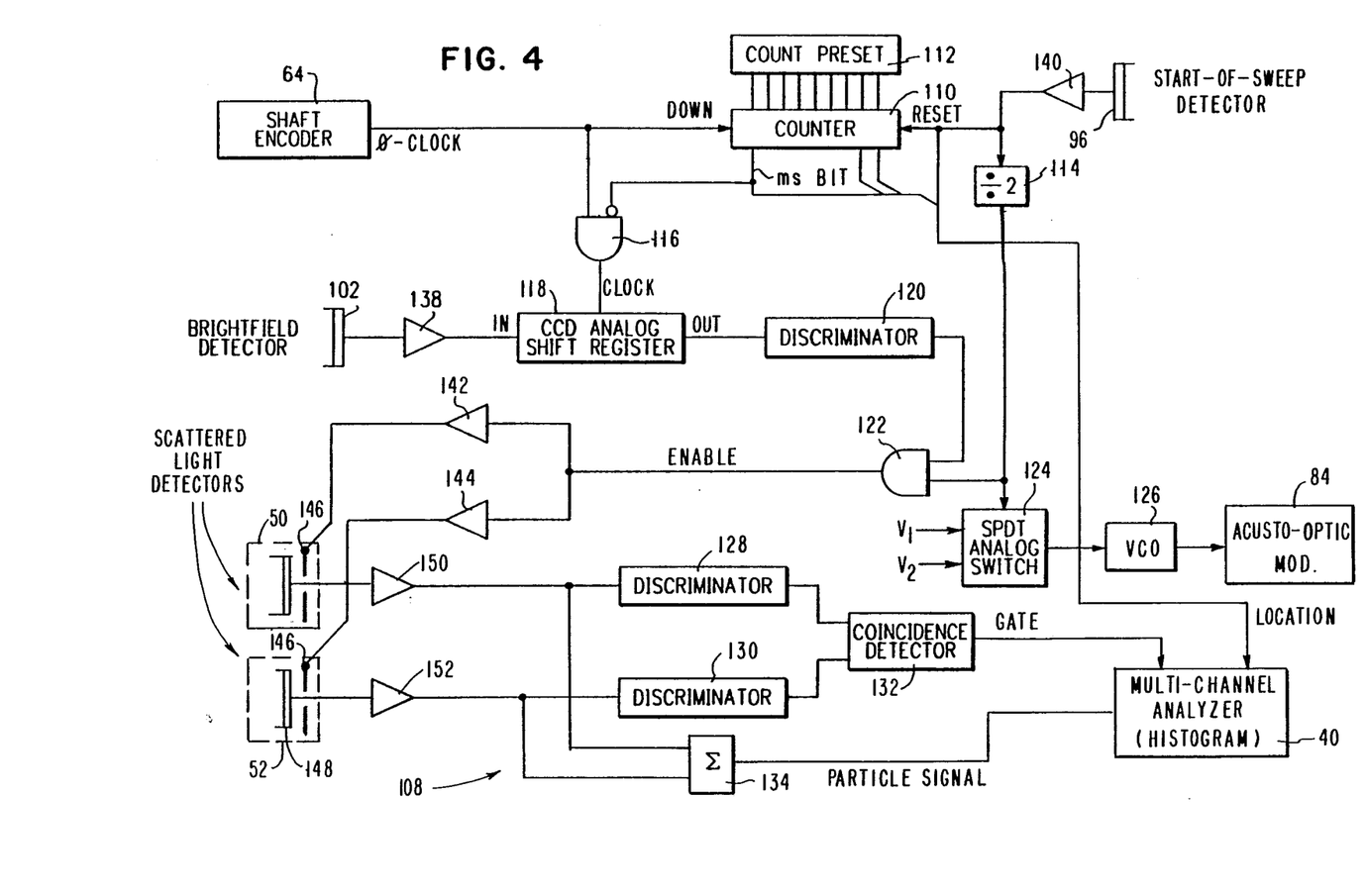
FIG. 4 is a schematic diagram of an electronics unit of the inspection system.

With reference also to FIG. 4, the scanner 22 further comprises an electronics unit 108 (also indicated in phantom in FIG. 1) having electrical circuitry and connections to components of the optical system 70 as shown in FIG. 4. Both the system 70 and the unit 108 are indicated in phantom within the scanner 22 of FIG. 1. FIG. 4 shows components of the optical system 70 previously described with reference to FIGS. 2 and 3, these components being the shaft angle encoder 64, the start-of-sweep photodetector 96, the detector 102 of the bright field of the laser beam, the scattered-light detectors 50 and 52, and the acousto-optic modulator 84. Also shown are connections to the analyzer 40 of FIG. 1. The electronics unit 108 comprises a counter 110 connected to a count-preset encoder 112, a frequency divider 114, an AND gate 116, a CCD (charge coupled device) analog shift register 118, an amplitude discriminator 120, an AND gate 122, a single-pole double-throw analog switch 124, a voltage-controlled oscillator (VCO) 126, a pair of amplitude discriminators 128 and 130, a coincidence detector 132 and a summer 134. In operation, the encoder 64 is mounted on a shaft 136 (FIG. 3) of the rotating mirror 60, and produces a pulse train at a repetition frequency dependent of the speed of rotation of the mirror 60. At the rotation speed in the preferred embodiment of the invention, the rate of occurrence of the pulses of the encoder 64 is such that approximately one pulse occurs for every 12 microns of travel of a spot of the scanned laser beam on the surface of the wafer 26. The train of pulses outputted by the encoder 64 serves as clock pulses for driving the counter 110 and the register 118. The clock pulses are connected directly to the counter 110, and are connected via the gate 116 to the register 118. While the register 118 may be of any desired size, in the preferred embodiment of the invention. the register 118 is provided with 16,384 cells.

The bright field detector 102 provides electric signals which are coupled via a buffer amplifier 138 to a data input terminal of the register 118. A data output terminal of the register 118 applies data samples to the discriminator 120. Upon each occurrence of a clock pulse applied via gate 116 to a clock input terminal of the register 118, the register 118 stores the input analog value of the signal outputted by the detector 102 in a first cell of the register 118. Signals stored in each of the cells are shifted to the next cell, and the signal of the last cell of the register 118 is outputted to the discriminator 120.

Data acquired by the detector 102 from specularly reflected light is stored in the register 118 with each scan of the scanned laser beam. Operation of the register 118 is synchronized with the scanning of the laser beam by means of the counter 110. The counter 110 is preset at the beginning of each scan with the number stored in the encoder 112 in response to a reset signal outputted by the detector 96. The signal outputted by the detector 96 is applied via a buffer amplifier 140 to a reset terminal of the counter 110. At the start of each scan, the counter 110 is preset to a count of 16,383. In response to the sequence of clock pulses from the encoder 64, the counter 110 counts down from the preset value until the count of the counter 110 becomes negative. Thereupon, the most significant bit (MSB) of the output count of the counter 110 becomes a logic-1. The MSB of the output count is applied to a complemented input terminal of the gate 116. Therefore, the MSB value of Logic-1 is converted to a logic-0 which deactivates the gate 116 to stop the flow of clock pulses to the register 118. This stops operation of the register 118. Upon resetting of the counter 110 for the next line scan, the MSB of the output count returns to a value of logic-0 to enable the gate 116 to resume passage of clock pulses to the register 118.

The train of reset pulses outputted by the detector 96 is applied also to the divider 114 which divides the repetition frequency of the pulse train by a factor of two. A train of pulses outputted by the divider 114 is applied to an input terminal of the gate 122 and to a control terminal of the switch 124. The gate 122 couples signals, outputted by the discriminator 120, via a pair of buffer amplifiers 142 and 144 to control grids 146 in the photomultiplier tubes of the detectors 50 and 52. The grids 146 interact with a light sensing electrode 148, a photocathode, in each of the photomultiplier tubes to prevent the outputting of a signal by the detectors 50 and 52 at all times except when the grids 146 are activated with suitable gate signals applied via the amplifiers 142 and 144 from the gate 122. It is the function of the amplitude discriminator 120 to distinguish the presence of differing intensities of reflections of the laser beam from the wafer surface so as to disable the detectors 50 and 52 in the presence of undulations in the wafer surface, and to enable the detectors 50 and 52 in the presence of a flat smooth wafer surface. Accordingly, the discriminator 120 outputs an enable gate pulse via the gate 122 to the control grids 146 in the presence of intense reflections, as will be described below, the enable gate pulses being manifested as a logic-1 signal outputted by the gate 122.

A feature of the invention is the pairing of scan lines such that a first line of each pair is employed for investigating the surface of the wafer 26 to determine which portions of the surface may generate intense reflections in the directions of the detectors 50 and 52, and which portions of the surface are flat and smooth so as to specularly reflect the laser beam back through the scan lens 58 without illuminating the detectors 50 and 52. In the case of the particle 90, the illumination of the detectors 50 and 52 is a low intensity scattered radiation. For example, it has been observed that surface metallization of the wafer 26 can create a reflected light beam with 10,000 times the scattered light intensity from a 10 micron spot on the wafer surface than a typical one-micron particle. During the second scan line of each pair of lines, the detectors 50 and 52 are activated to sense the scattered radiation associated with a particle such as the particle 90 on the wafer surface.

The requisite logic for accomplishing the foregoing procedures is accomplished by the discriminator 120, the divider 114, and the gate 122. The signal outputted by the divider 114 deactivates the gate 122 during the first line scan of each pair of line scans so as to prevent enablement of the detectors 50 and 52 during the initial investigation of the wafer surface. The signal outputted by the divider 114 activates the gate 122 to pass the enable signal from the discriminator 120 during the second scan line in each pair of scan lines. The register 118 stores a complete history of retroreflected light received at the detector 102 during the first scan line of the pair of scan lines. A strong signal stored in a cell of the register 118 indicates that substantially all of the laser light has been reflected back through the scan lens 58, this showing that a smooth flat region of the wafer surface is present at the specific location corresponding to the cell of the register 118 in which this information is stored. In the event that a cell of the register 118 stores a signal of reduced intensity, such reduced intensity is understood to be caused by undulations in a patterned region of the wafer surface. Such undulations may direct a major portion of the laser light at a direction inclined to a normal of the wafer surface resulting in a possible illumination of one of the detectors 50 and 52 with intense radiation. Accordingly, a reduced signal intensity stored in a cell of the register 118 is taken as an indication that the corresponding site on the wafer surface is not suitable for the viewing of particles by integrated scattered light within the hemisphere 48. The discriminator 120 is set to output an enable signal via the gate 122 for all retro-reflected optical signals having an intensity greater than a preset threshold intensity. For lower intensity signals, the discriminator 120 outputs a signal of the complementary logic state to disable the detectors 50 and 52.

Accordingly, for each scan line, the register 118 stores a complete record of the regions providing strong and weak reflections. In terms of odd and even scans, the odd scan being the first scan in each scan pair, and the even scan being the second scan in each pair, the data accumulated by the register 118 during an odd scan is outputted during the next even scan and evaluated by the discriminator 120 for enablement and disablement of the detectors 50 and 52. Data accumulated during an even scan in the register 118 is outputted during the next odd scan wherein the detectors 50 and 52 are disabled by the logic operation of the gate 122. Thus, data accumulated in the register 118 during even scans is discarded.

The switch 124 is activated by the signal outputted by the divider 114 to assume alternate ones of two possible switch states. Thereby, the switch 124 couples a voltage from a source $V_1$ to a control terminal of the oscillator 126 during each odd scan to select an oscillation frequency of the oscillator 126. During each even scan the switch 124 couples a voltage of a voltage source $V_2$ to the oscillator 126 to select an alternate oscillation frequency. The voltages of the two sources $V_1$ and $V_2$ have the requisite voltages for operating the oscillator 126 at the aforementioned frequency of 77.25 megahertz for the odd numbered scans, and at 77.23 for the even numbered scans. The oscillator 126 outputs a sinusoidal electric signal of the desired frequency to a control terminal of the acousto-optic modulator 84 to attain the desired beam deflections, one deflection being attained on the odd scans and the other deflection being attained on the even scans.

In the construction of the photomuliplier tubes of the detectors 50 and 52, the control grids 146 are operative with a voltage pulse of 5 volts, this being a convenient value for use with semiconductor logic circuitry such as the gate 122. The photomuliplier tubes can be gated on and off by logic pulses in a sufficiently short interval of time, typically a few nanoseconds, so as to enable a high resolution viewing of the surface of the wafer 26 during each scan line.

When the photomultiplier tubes are activated, the combination of the scattered light gathered by the integrating hemisphere 48 provides a measure of the total integrated scatter of laser light from the site of the wafer surface being viewed. Output signals of the detectors 50 and 52 are coupled via buffer amplifiers 150 and 152, respectively, to the discriminators 128 and 130. Output signals of the discriminators 128 and 130 are coupled via the coincidence detector 132 as a gate signal for operation of the analyzer 40. The use of plural detectors 50, 52 rather than a single detector, and the sensing of a coincidence in their signals provides immunity to noise in the light detection process. The output signals of the detectors 50 and 52 are also applied via the amplifiers 150 and 152 to the summer 134, the summer 134 summing together the signals of the detectors 50 and 52 to apply an analog signal representing the entire reflected radiation of the particle 90 to the analyzer 40.

Outputting of particulate data by the analyzer 40 is accomplished as follows. If the test site is free from particulate contaminants, the net scatter signal is relatively low, and the signals outputted by the detectors 50, 52 are below the amplitude threshold level of the discriminators 128 and 130. Hence, the discriminators 128 and 130 each output a logic-0 signal to the coincidence detector 132. If the laser light strikes a particle on the wafer surface, the total integrated light scatter within the hemisphere 48 is relatively high resulting in signals outputted by the detectors 50 and 52 which are above the amplitude threshold levels of the discriminators 128 and 130. Thus, each of the discriminators 128 and 130 output a logic-1 signal to the detector 132. The scattered light is sensed by both of the detectors 50, 52 at the same instant of time so as to cause the detector 132 to respond to the joint occurrence of logic-1 signals of the discriminators 128 and 130 by outputting a gate signal which enables the analyzer 40. In response to the gate signal of the detector 132, the analyzer 40 records the amplitude of the particle signal inputted to the analyzer 40 by the summer 134. The shaft angle encoder 64 outputs a train of pulses during each scan line, the number of pulses being equal to the number of cells of the register 118 into which the data of the detector 102 is to be stored. Since the same pulse train is applied to the counter 110, the count thereof is representative of the specific locations of a scan line which is being viewed by either the detector 102 or by the pair of detectors 50 and 52. Accordingly, the output count of the counter 110 is also applied to an input terminal of the analyzer 40 to indicate the location of the site of a particle on the wafer surface for which the particle signal of the summer 134 is being provided. Thereby, the analyzer 40 identifies the location of each particle and also shows the characteristic of reflected light from each particle. This information permits generation of a statistical analysis of the particulate contaminants both in terms of the reflectivity of the particles and the locations of the particles. It is noted that such information is obtained independently of the specific orientation of the wafer 26, there being no need to align a kerf region thereof with a scan line. Also, it is noted that information is attained from smooth flat areas which may be found occasionally within a patterned region as well as the more numerous flat surface areas found within a kerf region.

In the preferred embodiment of the invention, the inspection system 20 provides for a 195 millimeter field of view, which comprises a 12 micron-laser beam spot size by 16,384 pels (picture elements) per line. The scanner 22 can scan an 8 inch diameter wafer in 34 seconds, this being a distance of 200 millimeters which is viewed at a rate of 6 millimeters per second. The system 20 can detect unpatterned high reflectivity regions as small as 36 microns, this having an area equal to the size of 3 spots, and is capable of detecting particles in these regions equal to or larger than approximately 0.3 microns in diameter. The particle counts are accumulated and sorted by size, based on scattered light intensity, by the analyzer 40.

Figure 6:
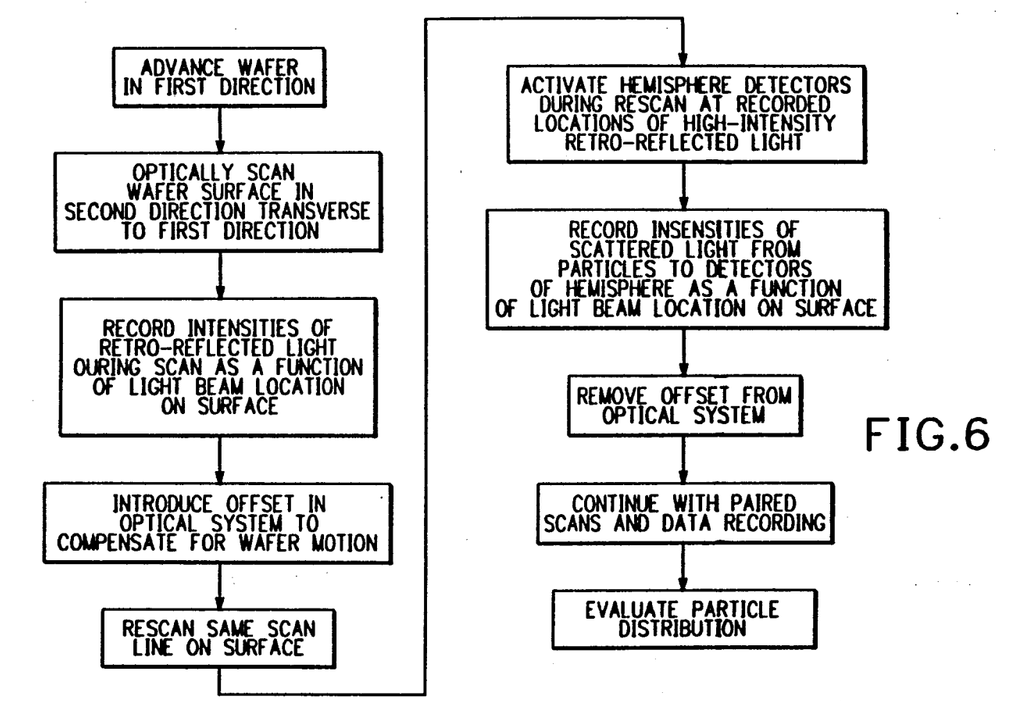
FIG. 6 is a block diagram showing method steps in the procedure by which the inspection system operates.

By way of summary of the operation of the inspection system 20, FIG. 6 shows the method steps in the operating procedure of the system 20. As set forth in FIG. 6, the wafer is made to advance in a first direction after which the surface of the wafer is optically scanned in a second direction, transverse to the first direction. the intensities of light retroreflected through the optical system 70 from the wafer surface during the scan are recorded in the shift register 118 as a function of light beam location on the wafer surface. Locations are given by the sequence of clock pulses emanating from the shaft angle encoder 64 connected to the rotating polygon mirror 60. There follows an introduction of an offset in the optical system to compensate for wafer motion, which offset is accomplished by the acousto-optic modulator 84. The wafer surface is then rescanned following the same path as the previous scan. The detectors 50 and 52 in the hemisphere 48 are then activated via the AND gate 122 at the locations in which high intensity retroreflections were obtained during the previous scan. There follows a recording of the intensities of scattered light from particulate contaminants as detected by the hemisphere detectors. The recording of data from the hemisphere detectors is accomplished as a function of light beam location on the wafer surface, the location being given by the count of the counter 110. Thereupon, the offset introduced by the acousto-optic modulator 84 is removed and the foregoing two scans are repeated to gather data about another region of the wafer. Upon completion of the scanning of the complete wafer, the particle data is evaluated by the analyzer 40.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. A surface inspection system for determining the presence of particles on the surface of a wafer, the surface having smooth and patterned regions, the system comprising:
    means for scanning said surface to locate smooth regions thereof;
    means coupled to said scanning means for sensing the presence of particles resting on said surface; and
    means for activating said sensing means, said activating means being responsive to surface data including locations of smooth regions outputted by said scanning means for activating said sensing means in the presence of smooth regions, and for deactivating said sensing means in the presence of patterned regions.

2. An inspection system according to claim 1 wherein said scanning means includes an optical system having an output lens assembly for illuminating said wafer surface with a beam directed normally to said surface, said optical system including means for extracting rays of said beam reflected normally from said surface to sense a smoothness of said surface.

3. An inspection system according to claim 2 wherein said optical system includes means for focusing extracted rays of said beam to obtain an image of said surface, thereby to distinguish a flat surface from elevations and depression at altitudes different from a reference altitude of said surface, flat smooth regions of said surface being at said reference altitude.

4. An inspection system according to claim 2 wherein said scanning is accomplished as a set of parallel scan lines; and wherein
    said scanning means includes a conveyor means for transporting the wafer past said lens assembly in a direction transverse to said scan lines; and wherein said scanning means includes means for offsetting alternate scan lines to compensate for movement of said wafer to provide pairs of identical scan lines.

5. An inspection system according to claim 4 wherein said activating means comprises driving means and memory means, said driving means driving said memory means to store surface data outputted by said scanning means during a first scan of each pair of scan lines, said driver means operating said sensing means to sense particles only during a second scan line of each pair of scan lines.

6. An inspection system according to claim 5 wherein data stored in said memory means during a first scan line of said pair of scan lines is outputted by said memory means during a second scan line of said pair of scan lines, and wherein said driving means is activated by said outputted data to gate said sensing means at specified locations designated by the data outputted from said memory means.

7. An inspection system according to claim 6 wherein said driver means includes discriminating means for evaluating data outputted by said memory means during said second scan line, said driver means including logic means responsive to signals outputted by said discriminator means to accomplish said gating of said sensing means.

8. An inspection system according to claim 7 wherein said sensing means includes a reflecting hemisphere for integration of radiant energy in rays of radiation reflected from one of said particles; and wherein
    said optical system includes means for imparting circular polarization to radiation of said beam for improved detection of said particles.

9. An inspection system according to claim 8 wherein said sensing means includes a plurality of detectors of radiant energy directed inwardly of said hemisphere for reception of rays of radiant energy reflected within said hemisphere, each of said detectors being gated by said driver means.

10. An inspection system according to claim 1 wherein said smooth regions are flat, and wherein said sensing means includes a reflecting hemisphere for integration of radiant energy in rays of radiation reflected from one of said particles; and wherein
    said sensing means includes a plurality of detectors of radiant energy directed inwardly of said hemisphere for reception of rays of radiant energy reflected within said hemisphere; and wherein
    said optical system includes means for imparting circular polarization to radiation of said beam for improved detection of said particles.

11. A surface inspection system for determining the presence of particles on the surface of a workpiece, the surface having smooth and patterned regions, the system comprising:
    means for scanning said surface in a sequence of paired line scans, each pair of line scans including a first scan and a second scan identical to said first scan;
    a surface sensor operatively coupled to said scanning means for distinguishing between features of the surface;
    a particle sensor operatively coupled to said scanning means for detecting the presence of a particle resting on the surface; and
    activating means operating concurrently with said scanning means for receiving data of features of the surface from said scanning means and said surface sensor during said first scan in each pair of line scans, said activating means activating said particle sensor during said second scan in each pair of line scans to be responsive to the presence of a particle located on a flat smooth region of the surface, said activating means deactivating said particle sensor in the absence of a flat smooth region of the workpiece surface.

12. An inspection system according to claim 11 wherein said surface features include flat regions and patterned regions, said surface sensor including means for discriminating between flat and patterned regions.

13. An inspection system according to claim 11 wherein said scanning means comprises conveyor means for conveying a workpiece in a direction transverse to the direction of a line scan, and means for offsetting said second line scan to compensate for movement of said conveyor means such that said second line scan coincides with said first line scan.

14. A surface inspection system according to claim 13 wherein said surface sensor comprises optical beam focusing means including lens elements and an acousto-optic modulator positioned serially with lens elements of said focusing means; and wherein
said line offset means comprises means for generating acoustic signals at a plurality of frequencies for driving said modulator to deflect a beam of radiation propagating through said optical focusing means to said surface, there being individual ones of said acoustic frequencies corresponding to selected offset directions of said beam.

15. An inspection system according to claim 11 wherein said activating means comprises a memory for storing location data received from said scanning means, said location data providing the locations of positions on said surface scanned within said first scan, said memory being coupled to said surface sensor for storing signals of radiant energy reflected from said surface to designate a type of surface present at each of said locations.

16. An inspection system according to claim 11 wherein said surface sensor comprises a laser and optical beam focusing means successively scanning beams of said laser across the surface of said workpiece, said focusing means directing said beam normally to said workpiece surface, and wherein said focusing means comprises beam splitting means for receiving retroreflected rays from said surface and detecting means operatively coupled to said beam splitting means for detecting retroreflected rays of radiation, said detecting means including a lens and a pinhole for producing a confocal sensing of the surface.

17. An inspection system according to claim 16 wherein said particle sensor comprises a hemispherical reflector enclosing said workpiece, there being a plurality of photomultiplier tubes extending inwardly of said hemispherical reflecting surface for viewing energy of rays scattered from a particle on the workpiece surface.

18. An inspection system according to claim 17 wherein said beam focusing means comprises a scanning mirror in optical alignment with said beam splitter means, there being a quarter waveplate producing circular polarization disposed between said scanning mirror and said beam splitting means for polarizing a beam of radiation emanating from said laser.

19. An inspection system according to claim 18 wherein said surface sensor and said particle sensor are optically coupled to said beam focusing means, said surface sensor and said particle sensor each comprising a discriminator for comparing amplitude of received radiation with a threshold, and wherein said particle sensor further comprises a coincidence detector for detecting coincidence between optical signals received at each of said photomultiplier tubes.

20. An inspection system according to claim 18 wherein said scanning means comprises a shaft angle encoder, and wherein said activating means comprises an analog shift register and a counter, said shaft angle encoder being coupled to said scanning mirror and providing clock pulses for driving said shift register and said counter, said counter providing a series of counts measuring locations along a line scan, said shift register being coupled to said surface sensor for storing data reflected from the workpiece surface at locations designated by a count of said counter.

21. An inspection system according to claim 20 further comprising means coupled to said activating means and to said particle sensor for displaying amounts of energy reflected from a particle upon the workpiece surface and the locations of such reflections.

22. A method of inspecting a surface of a workpiece to determine the presence of particles thereon, the method comprising the steps of:
advancing the workpiece in a first direction;
optically scanning a surface of the workpiece in a second direction transverse to a said first direction, said optical scanning employing a beam directed perpendicular to the surface of the workpiece;
obtaining gross surface data in the form of locations of undulations and flat portions of the surface of the workpiece;
repeating a scan of the workpiece surface to cover the same region covered by the first scan of the workpiece surface;
obtaining particle data by light reflected from a particle on the workpiece surface at locations of flat portions of the surface obtained from the gross data; and
continuing with the advance of the wafer in the first direction and the scanning in the second direction to obtain further data of the surface of the workpiece.

* * * * *